United States Patent [19]

Moyer

[11] 4,022,893
[45] May 10, 1977

[54] TREATMENT FOR HYPERTENSION

[76] Inventor: John H. Moyer, 556 Colgate Ave., Johnstown, Pa. 15905

[22] Filed: Jan. 24, 1975

[21] Appl. No.: 543,697

[52] U.S. Cl. .................................. 424/246; 424/330
[51] Int. Cl.² ................ A61K 31/54; A61K 31/135
[58] Field of Search ............................ 424/330, 246

[56] References Cited
OTHER PUBLICATIONS

Davis–Chem. Abst., vol. 75, (1971), p. 47191b.
Sjoerdsma–Chem. Abst., vol. 70, (1969), p. 36408y.
Korczyn et al.–Chem. Abst., vol. 80, (1974), p. 128,368v.
Baisset et al.–Chem. Abst., vol. 79, (1973), p. 61733u.

*Primary Examiner*—Sam Rosen
*Attorney, Agent, or Firm*—Jackson, Jackson & Chovanes

[57] ABSTRACT

A treatment for hypertension by the conjoint use of phenoxybenzamine and propranolol, desirably with the conjoint use also of a diuretic.

9 Claims, No Drawings

TREATMENT FOR HYPERTENSION

DISCLOSURE OF INVENTION

My invention relates to treatment for hypertension by the conjoint use of propanolol and phenoxybenzamine, desirably with the conjoint use also of a diuretic.

A purpose of my invention is to treat hypertension, especially ordinary hypertension or essential hypertension, by the conjoint use of propranolol and phenoxybenzamine.

A further purpose is to add also a diuretic.

A further purpose is to treat hypertension which resists other treatments by the reagents specified.

Propranolol is 1-(isopropylamino)-3-(1-naphthyloxy)-2-propanol, and it is described in medical dictionaries and the like.

Phenoxybenzamine is N-(2-chloroethyl)-N-(1-methyl-2-phenoxyethyl) benzylamine, and it is also described in medical dictionaries.

Hypertension is a serious condition. For example, an average person at the age of 35 who has a blood pressure of 150/100 mm, his life expectancy is reduced about 15 years. If he has malignant high blood pressure which means not that he has cancer or anything like that, but merely that the amount of blood pressure is very much increased, the mortality untreated is usually 90% in 2 years and 100% in 5 years.

Ordinary high blood pressure is hard to describe. The medical dictionaries use a term "idiopathic" but that term is not in normal use. The term for ordinary high blood pressure is essential hypertension. This name arose from the fact that at one time it was thought that for that particular patient the high blood pressure was "essential" because otherwise he would not maintain the flow of blood through the brain and of course would die. This theory turned out to be completely erroneous, but the terminology of essential hypertension is still in good use for ordinary hypertension.

Another form of terminology is diastolic hypertension which was on the theory that the distinguishing characteristic of this type of high blood pressure was the fact it was present in the diastolic phase of heart contraction whereas other high blood pressure was present only in the systolic condition. However, this terminology proved also to be a misnomer since high blood pressure occurs both in the diastolic and systolic mode in the ordinary case so that the term is of no use.

Malignant high blood pressure is a term used when the blood pressure is very high, not to imply that the patient has any malignancy or the like. The physician usually diagnoses and defines malignant high blood pressure by looking into the retina of the eyes and if he sees fluid in the optic nerve head and hemorrhaging in the retina, he diagnoses malignant high blood pressure.

In the present invention the term essential high blood pressure will be used for ordinary high blood pressure or blood pressure which is high without any apparent cause.

Patients are individuals, and many patients have blood pressure which is high but it does not require extraordinary measures to lower it, and this invention particularly will be applied when the patient has blood pressure which eludes normal treatment.

METHOD OF TREATMENT

In the method of treatment prescribed by the present invention, the first thing is to give a diuretic, preferably hydrochlorothiazide or a diuretic of similar action which may be administered at the rate of about 100 mg. per day, preferably in two doses. Any other thiazide diuretic may be administered in equivalent therapeutic amount, such as the thiazide diuretics contained in Table 2 of Drug Treatment of Ambulatory Patients with Hypertension, American Medical Association Journal for Sept. 24, 1973, Volume 225, No. 13, pages 1647–1653, the table appearing on page 1649. As an alternative for the thiazide diurectics ethacrynic acid may be administered at the rate of 100 mg. per day in two doses. Ethacrynic acid is (2,3-dichloro-4-(2-methylenebutyryl) phenoxy) acetic acid. In many cases the administration of the diuretic will be sufficient, and nothing else need be given to control the high blood pressure. Similar results may be obtained with furosemide in a dose of 80 mgm./day.

If the high blood pressure fails to lower sufficiently under treatment of the diuretic, then 40 mg. per day of propranolol (10 mgm. given four times a day) in addition to the diuretic may be administered increasing the dose to 80 mg. given four times a day. This dose is gradually increased so that by the third week 40 mg. are administered four times a day. By the fourth to sixth week 80 mg. of propranolol is administered four times per day along with the diuretic.

If the blood pressure still fails to come down sufficiently, then dibenzyline is administered with the diuretic and the propranolol. Dibenzyline is phenoxybenzamine or N-(2-chloro-ethyl)-N-(1-methyl-2-phenoxyethyl) benzylamine. By the fifth week or there abouts in addition to the diuretic and 80 mg. of propranolol given four times a day, 2.5 mg. of dibenzyline is administered daily. A combination tablet of 10 mg. of propranolol and 2.5 mg. of dibenzyline may be used so as to reduce the number of tablets the patient must take.

If the blood pressure does not come down sufficiently, then on the sixth week or there abouts, the daily dose of diuretic and propranolol are maintained and dibenzylene is increased. The drugs are administered daily. These are given in combination tablets with the appropriate ratios.

If the blood pressure has not come down sufficiently, in the the seventh week, the diuretic and 80 mg. of propranolol give four times a day are administered and combination tablets totaling 30 mg. of propranolol and 7.5 mg. of dibenzyline are administered daily.

If the blood pressure has still not been reduced sufficiently by the eighth week, then 100 mg. of diuretic daily and the 80 mg. of propranolol are given four times a day. Then 10 mg. of dibenzyline is administered daily.

This process goes on increasing the propranolol and dibenzyline until 80 mg. of propranolol are administered four times a day and a maximum of 60 mg. of dibenzyline are administered conjointly optionally in tablets with ratios of 10 mg. of propranolol and 2.5 mg. of dibenzyline and 40 mg. of propranolol and 10 mg. of dibenzyline daily which are administered in a single tablet as well as 20 mg. of propranolol and 5 mg. of dibenzyline in the same tablet. This maximum administered dose per tablet is 80 mg. propranolol and 10 mg. of dibenzyline.

As far as the quantities of propranolol and dibenzaline are concerned, the present invention involves administering them in a quantity not exceeding 360 mg. daily of propranolol and not exceeding 60 mg. daily of dibenzyline.

RATIONALE OF TREATMENT

The rationale of this treatment is that the diuretic prevents fluid buildup and tolerance to blood pressure increases. The propranolol prevents tachycardia, that is, massive side effects from the dibenzyline which would speed up the heart beat. Dibenzyline is an alpha-adrenergic block on the effect of the sympathetic nervous system on the blood vessels directly and propranolol is a beta-adrenergic block which acts directly on the sympathetic nervous system in regard to that system's action on the heart. The combined effect is blockage as to both the blood vessels and the heart, allowing the patient's body to act normally in both the blood vessels and the heart and thus give normal conditions which are desired instead of unduly rapid heart beat.

Prior Art

In the prior art in the comparatively rare condition of pheochromocytoma which may be a tumor which occurs on the medulla of the adrenal gland or in the thorax, a synonym of which is pheocromoblastoma, the use of propranolol and dibenzyline has been prescribed to correct excessive amounts of catecholamines which result in inotropic or chronotropic effects which would speed up or strengthen the heart. Physicians' Desk Reference, 1973, pages 570-571. These drugs reduce the effect of excessive hypertension before and during the treatment of surgery of the tumor diminishing the effect of cardiac stimulation by catecholamines. This is an entirely different purpose than the invention contemplates.

EXAMPLES

In all cases in the examples 100 mg. of the diuretic hydrochlorothiazide was administered in two doses daily throughout.

Case 1

This is a male of 55 years of age who had an initial blood pressure of 230/140.

The diuretic in two weeks reduced this blood pressure to 200/130. This reduction of course was not enough. On the third week in addition to the diuretic, 40 mg. of propranolol was administered in four daily doses. In the fourth week 80 mg. of propranolol was administered daily additionally to the diuretic.

In the fifth week in addition to the above administration, one tablet having 2.5 mg. of dibenzyline was administered in addition to the propranolol and diuretic daily at one time.

In the sixth week in addition to the diuretic and the 80 mg. of propranolol 5 mg. of dibenzyline was administered in two daily doses.

In the seventh week the diuretic and the 80 mg. of propranolol were continued and 10 mg. of dibenzyline was administered daily.

In the eighth week in addition to the diuretic and the 80 mg. of propranolol, 2.5 mg. of dibenzyline was administered. This progression continued until the diuretic and 160 mg. total of propranolol and 20 mg. of dibenzyline were administered each day. At that point the blood pressure was 120/88. The side effects were mild lethargy, clearing after one month of continued therapy.

Case 2

Case 2 is a male 50 years old who had originally a blood pressure of 180/120. Placed on a diuretic for two weeks, his blood pressure at the end of this period was 170/120. On the third week he was given propranolol 40 mg. daily four times a day increased to 80 mg. daily in the second week, at the end of which time his blood pressure was still 170/120. In the fourth week he was given 80 mg. of propranolol four times a day. In the fifth week the diuretic and the 80 mg. of propranolol still being administered, he was also given 2.5 mg. of dibenzyline daily gradually increasing week to week until he received a total 240 mg. of propranolol and 30 mg. of dibenzyline daily at which time his blood pressure stabilized at 138/90. No side effects were noted.

Case 3

This case is a female 46 years of age who originally had a blood pressure of 170/110. After administering a diuretic as above for two weeks, she had a blood pressure of 170/112. After administering propranolol in increasing amounts in addition to the diuretic for two weeks (80 mg. daily of propranolol was administered for the fourth week) her blood pressure was 160/102. Then, still administering 100 mg. of diuretic daily and propranolol and 2.5 mg. of dibenzyline were increased until the daily dose was 80 mg. of propranolol and 10 mg. of dibenzyline. Her blood pressure was stabilized at 120/80. There was mild weakness as a side effect.

Case 4

Case 4 is a female of 55 years of age who had a blood pressure initially of 180/120. After administering a diuretic in daily doses of 100 mg., her blood pressure was 170/116. On the third and fourth weeks propranolol was administered in addition to the diuretic in daily doses of first 40 mg. and then 80 mg. given four times a day at the end of which the blood pressure was 160/106.

Then in addition to the 100 mg. of diuretic and 80 mg. of propranolol increasing dosage starting at 2.5 mg. daily of dibenzyline increasing to 80 plus 80 mg. of propranolol and eventually 10 mg. of dibenzyline was administered simultaneously in simultaneous daily doses using tablets of 40 mg. of propranolol and 2.5 mg. of dibenzyline. The blood pressure stabilized at 112/70. The result was characterized by marked fatigue, lethargy and apathy and occasional dizziness on standing.

Case 5

This case is a male 42 years of age and originally he had a blood pressure of 190/118. After administering a diuretic for two weeks in a standard amount of 100 mg. per day in two doses, he patient's blood pressure was 180/106.

Then in addition to the diuretic, propanolol was administered for two weeks in daily doses starting at 40 mg. of propranolol and ending at 80 mg. of propranolol in daily doses. The patient's blood pressure was 168/108 at the end.

Then the administration of diuretic was continued and 80 mg. daily of propranolol plus simultaneous administration of dibenzyline starting at 2.5 mg. of dibenzyline and rising until the amount of dibenzyline was 80 mg. of propranolol and 20 mg. of dibenzyline administered daily simultaneously in four doses. As a side effect the patient experienced some impotency.

Case 6

Case 6 is a male of 52 years of age who originally had a blood pressure of 210/124. After administering a diuretic in daily doses of 100 mg. for two weeks, the patient's blood pressure was 180/120. In the third and fourth weeks in addition to the diuretic, propranolol was administered first at 40 mg. per day and then at 80 mg. per day. The patient's blood pressure was then 170/114.

Then the propranolol was increased and dibenzyline was administered until ultimately the total amount of propranolol was a daily dose of 140 mg. and 30 mg. of dibenzyline.

The patient's blood pressure stabilized at 140/100. No side effects occurred.

In view of my invention annd disclosure, variations and modifications to meet individual whim or particular need will doubtless become evident to others skilled in the art, to obtain all or part of the benefits of my invention without copying the method and composition shown, and I therefore claim all such insofar as they fall within the reasonable spirit and scope of my claims.

Having thus described my invention, what I claim as new and desire to secure by Letters Patent is:

1. The method of treating essential hypertension in human beings, which comprises administering concomitantly effective amounts of phenoxybenzamine and propranolol in a quantity not exceeding 60 mg. daily of phenoxybenzamine and not exceeding 360 mg. daily of propranolol.

2. The method of claim 1, in which there is concomitantly also administered a diuretic.

3. The method of treating hypertension in humans, which consists of administering first hydrochlorothiazide in the quantity of 100 mg. per day, administering in effective amounts simultaneously propranolol and dibenzyline in a quantity not exceeding 360 mg. daily of propranolol and not exceeding 60 mg. daily of dibenzyline.

4. A tablet for conjoint use containing 10 mg. of propranolol and 2.5 mg. of dibenzyline.

5. A tablet for conjoint use ccontaining an effective amount of hydrochlorothiazide along with the ingredients indicated in claim 4 above.

6. A tablet for conjoint use consisting of 40 mg. of propranolol and 10 mg. of dibenzyline.

7. A tablet for conjoint use containing an effective amount of hydrochlorothiazide along with the ingredients indicated in claim 6 above.

8. A tablet for conjoint use containing 80 mg. propranolol and 10 mg. dibenzyline.

9. A tablet for conjoint use containing an effective amount of hydrochlorothiazide along with the ingredients indicated in claim 8 above.

* * * * *